(12) United States Patent
Thorson

(10) Patent No.: US 7,093,303 B2
(45) Date of Patent: *Aug. 22, 2006

(54) PERSPIRATION BLOCKING AND ABSORBING APPARATUS

(76) Inventor: Bjorne Paul Thorson, 3250 County Road 67, Colorado Springs, CO (US) 81240

(*) Notice: Subject to any disclaimer, the term of this patent is extended or adjusted under 35 U.S.C. 154(b) by 0 days.

This patent is subject to a terminal disclaimer.

(21) Appl. No.: 10/888,346

(22) Filed: Jul. 9, 2004

(65) Prior Publication Data

US 2005/0132477 A1 Jun. 23, 2005

Related U.S. Application Data

(63) Continuation-in-part of application No. 10/314,144, filed on Dec. 9, 2002, now Pat. No. 6,789,272.

(51) Int. Cl.
*A61F 9/00* (2006.01)

(52) U.S. Cl. .................... 2/13; 2/12; 2/181; 2/DIG. 11; 351/62

(58) Field of Classification Search ................ 2/181.2, 2/181.4, 181.6, 181.8, 182.3, 182.4, 182.5, 2/426, 181, 431, 13, 452, 453, 12, 438, 448, 2/450, DIG. 11; 351/62, 123, 156, 155, 157, 351/44

See application file for complete search history.

(56) References Cited

U.S. PATENT DOCUMENTS

| 703,531 | A | * | 7/1902 | Brown | 2/171 |
|---|---|---|---|---|---|
| 1,462,532 | A | * | 7/1923 | Bonner | 2/12 |
| 1,585,023 | A | * | 5/1926 | Fant | 2/13 |
| 2,393,837 | A | * | 1/1946 | Swanson | 351/62 |
| 2,491,216 | A | * | 12/1949 | Schlumbohm | 2/12 |
| 2,580,744 | A | * | 1/1952 | Edsall | 2/13 |
| 3,133,982 | A | * | 5/1964 | Janz | 351/62 |
| 3,578,736 | A | * | 5/1971 | Dootson | 2/181 |
| 3,874,776 | A | * | 4/1975 | Seron | 351/123 |
| 4,393,519 | A | * | 7/1983 | Nicastro | 2/12 |
| 4,446,571 | A | * | 5/1984 | Ross | 2/13 |
| 4,502,156 | A | * | 3/1985 | Wishman | 2/181 |
| 4,549,793 | A | * | 10/1985 | Yoon | 351/156 |
| 4,616,367 | A | * | 10/1986 | Jean et al. | 2/452 |
| 4,621,378 | A | * | 11/1986 | Hatchman | 2/9 |
| 4,626,247 | A | * | 12/1986 | Frankel | 604/312 |
| 4,856,116 | A | * | 8/1989 | Sullivan | 2/181 |
| 4,934,807 | A | * | 6/1990 | Bolle et al. | 351/62 |
| 5,009,496 | A | * | 4/1991 | Holtan et al. | 351/156 |
| 5,032,018 | A | * | 7/1991 | McCulley et al. | 351/156 |
| 5,056,163 | A | * | 10/1991 | Chou | 2/453 |
| 5,146,630 | A | * | 9/1992 | Richard | 2/181 |
| 5,384,605 | A | * | 1/1995 | Escobosa | 351/123 |
| 5,428,844 | A | * | 7/1995 | Dougherty | 2/209.13 |
| 5,822,799 | A | * | 10/1998 | Kepple | 2/183 |

(Continued)

OTHER PUBLICATIONS

Airarc.com website, pp. 5-6, including Browmount and DryBrow(TM) Sweatbands.*

(Continued)

*Primary Examiner*—Rodney M. Lindsey
(74) *Attorney, Agent, or Firm*—Holme Roberts & Owen LLP

(57) ABSTRACT

The present apparatus is directed, in one embodiment, towards a liquid-absorbing component for attachment to eyeglasses, that impedes the flow of perspiration and other materials into the wearer's eyes. In another embodiment, the apparatus includes a liquid-absorbing component that is attachable to eyeglass arms and may be used independently of eyeglasses.

28 Claims, 5 Drawing Sheets

U.S. PATENT DOCUMENTS

| | | | | |
|---|---|---|---|---|
| 5,867,834 A | * | 2/1999 | Simpson | 2/174 |
| 5,887,284 A | * | 3/1999 | Simmons | 2/181.4 |
| 6,026,518 A | * | 2/2000 | Brown | 2/439 |
| 6,138,280 A | * | 10/2000 | Bae | 2/181 |
| 6,282,727 B1 | * | 9/2001 | Lindahl | 2/428 |
| 6,450,640 B1 | * | 9/2002 | Van Rysselberghe | 351/123 |
| 6,567,991 B1 | * | 5/2003 | Holslag et al. | 2/181.4 |
| 6,789,272 B1 | * | 9/2004 | Thorson | 2/426 |
| 2002/0100107 A1 | * | 8/2002 | Shin | 2/181 |
| 2003/0041365 A1 | * | 3/2003 | Sanchez | 2/181.6 |

OTHER PUBLICATIONS

Emergency Response—Outdoor Protection Product Brochure, p. 2, including MiraCool (TM) Terry Coolers and Terri-Band (TM) Sweatband.*

VillageHatShop.com website, p. 4, including Cap-Ban-Nu Disposable Sweatband.*

Omark Safety Online website, 6 pages.* www.westernsafety.com pp. 1-3.*

Emergency Response—Outdoor Protection—Disposable Sweatbands.* www.safety-products.com/store/items.asp?GROUP ID=3036.* www.sharpesafety.com/catalog/product-display.php3?ID=7.* www.omarksafety.com/category.cfm/acatid-29-aprodid-194-Drybrow$_{13}$Sponge_Swea . . . .* www.airarc.com/products/safety/huntsman.html pp. 1-6.* www.bd.com/clinical/POL/products/equipment/drybrow.asp.* www.pro-am.com/Catalog/Exec/product.asp?product_id=170.* www.pro-am.com/Catalog/Exec/search_cat.asp?cat_2=36.* www.safety-wear.com/shop/item/econodrybrowsweatband.html.* www.safety-products.com/store/.* www.safety-products.com/store/items.asp?GROUP_ID=2137.*

The present inventor has described having seen in private use a foam rubber strip with holes in each end of the strip for inserting the arms of eyeglasses, developed by his father, Bennie Thorson, with the present inventor also contributing to development. This could be deemed to be prior art but we assert it is not.*

WWW.METTAM.COM.*

* cited by examiner

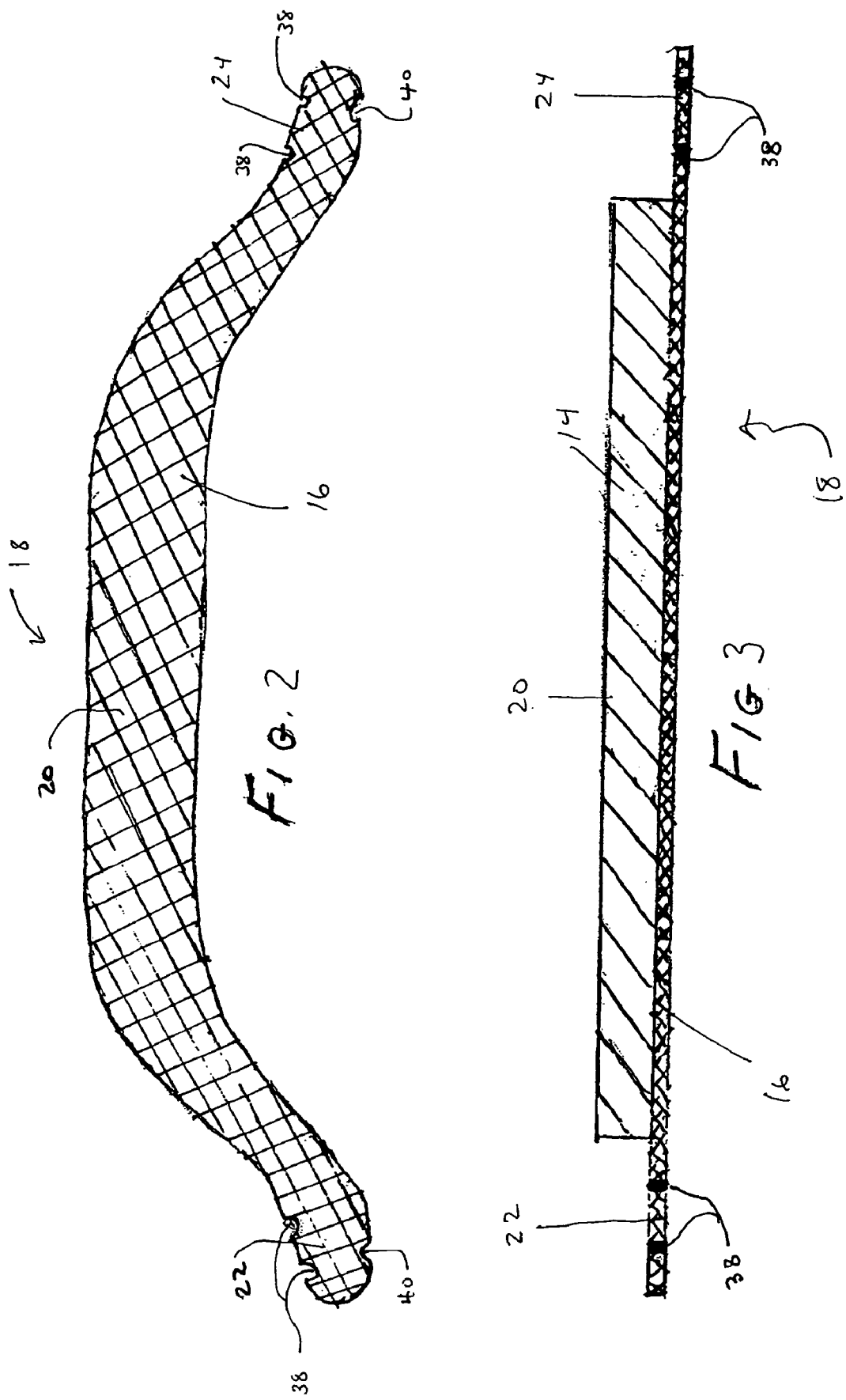

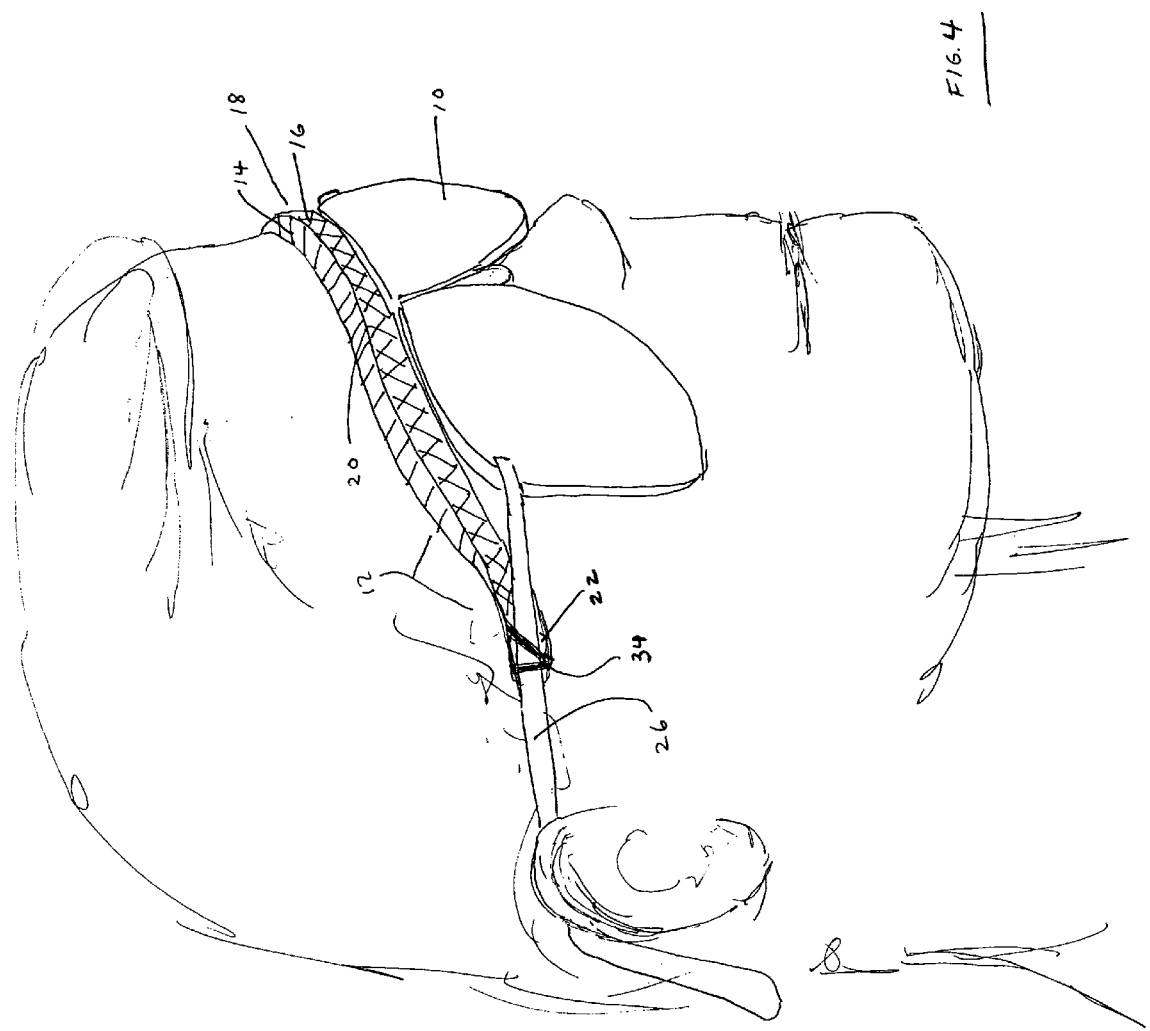

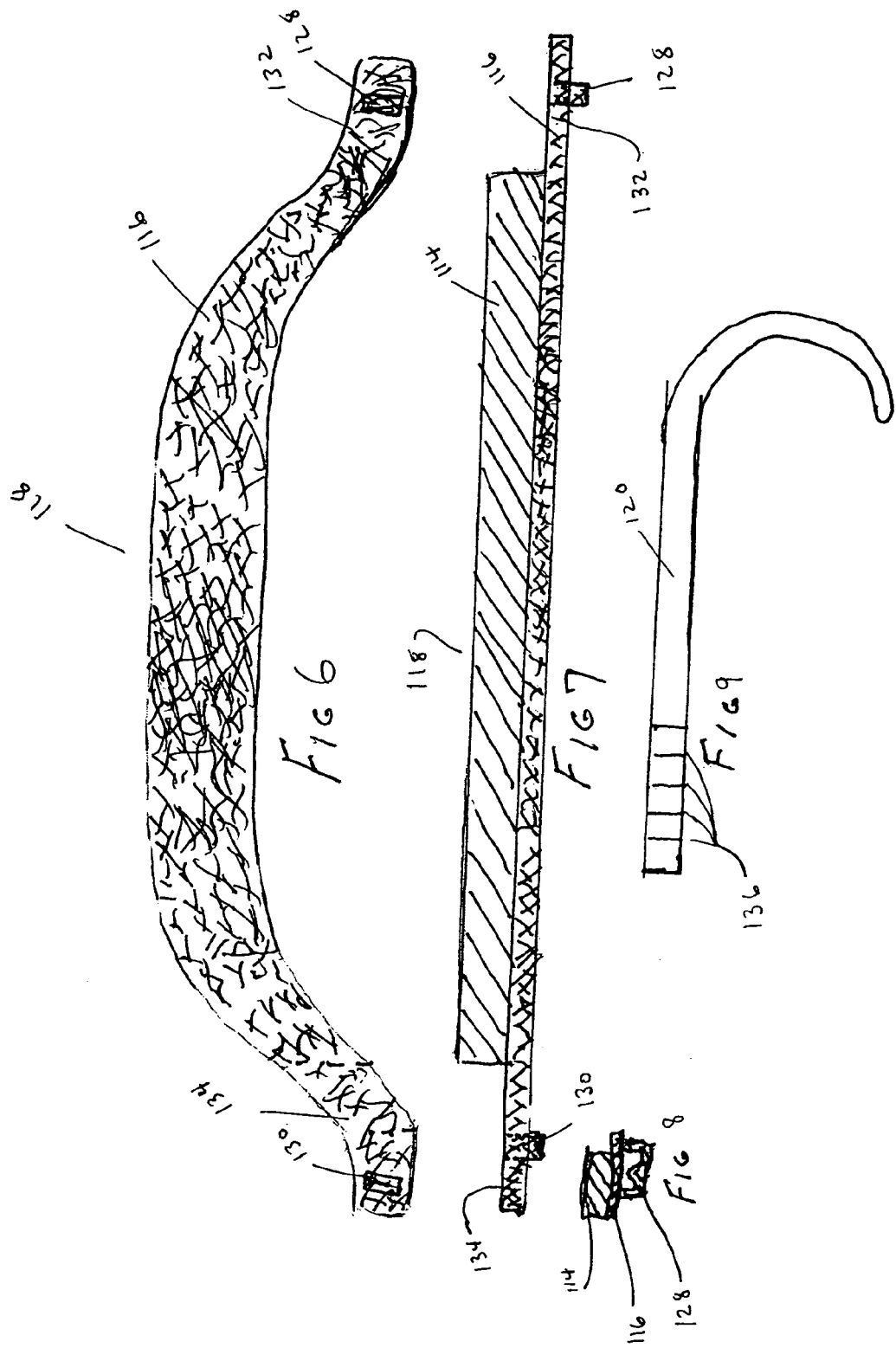

PERSPIRATION BLOCKING AND ABSORBING APPARATUS

CROSS REFERENCES

The present application is a continuation-in-part of application Ser. No. 10/314,144 entitled EYE GLASS PERSPIRATION GUARD, filed in the U.S. Patent and Trademark Office on Dec. 9, 2002 now U.S. Pat. No 6,789,272.

BACKGROUND

1. Field

The field includes devices for impeding the flow of and absorbing perspiration on a wearer's forehead.

2. Related Art

Various sweat bands have been developed for wear on the forehead. These generally involve a single piece of cloth, foam rubber, or other absorbent material, often stretchable, that encircles the wearer's head. In some cases, a stretchable string or strap extending around the back of the wearer's head is used to tie the piece of absorbent material on the wearer's head. Sweat bands that have material extending around the wearer's head tend to interfere with wearing of hats, hardhats, goggles and eyeglasses. Strips of sweat-absorbing material have been configured for attachment to the rim of eyeglasses and goggles above the wearer's nose and the lenses of the eyeglasses. These strips are often not maintainable in close contact with the user's forehead because they are attached to the rims of the eyeglasses, which may slip down the wearer's nose. Sweat bands also have been designed to be attached to the inner lining of hats. These often are positioned too high on the forehead to block sweat forming immediately above the wearer's eyes. Headbands completely encircling the wearer's head have been designed to be attached to and support eyeglasses, but often interfere with wearing hats, hardhats and other head coverings.

SUMMARY

BRIEF DESCRIPTION OF THE DRAWINGS

FIG. 2 is a front view of the component of the embodiment of FIG. 1, depicting the second piece.

FIG. 3 is a cross-sectional view of the component of the embodiment of FIG. 1.

FIG. 4 is a front perspective view of the embodiment of FIG. 1, showing the embodiment worn on the head of a person.

FIG. 6 is a front view of the component of the embodiment of FIG. 5, depicting the second piece.

FIG. 7 is a cross-sectional view of the component of FIG. 6.

FIG. 8 is an enlarged cross sectional view of one attachment means of the embodiment shown in FIG. 7.

FIG. 9 is a side view of one arm of the embodiment of FIG. 5.

DETAILED DESCRIPTION

The present apparatus is especially advantageous for persons who wear eyeglasses, safety glasses or goggles, but is not limited to these applications.

This description incorporates by reference the information provided in U.S. Patent Office application of Bjorne Paul Thorson, application Ser. No. 10/314,144 having a filing date Dec. 9, 2002.

In a first embodiment depicted in FIGS. 1, 2, 3, and 4, useable with eyeglasses 10, or alternatively with safety glasses or goggles, the apparatus 12 includes a first piece 14 of material, preferably formed of an elongated sheet of liquid-absorbent material such as foam rubber. The device also includes a second piece 16 formed of an elongated sheet of material such as plastic, the second piece 16 being of about the same size and shape as the first piece 14, and the first piece 14 and the second piece 16 being connected together by connecting means such as by a glue or other adhesive like cyanoacrylate. The second piece 16 serves to provide support to the first piece 14 and also provides a means for attaching the first piece 14 to eyeglasses 10.

Figure 1:
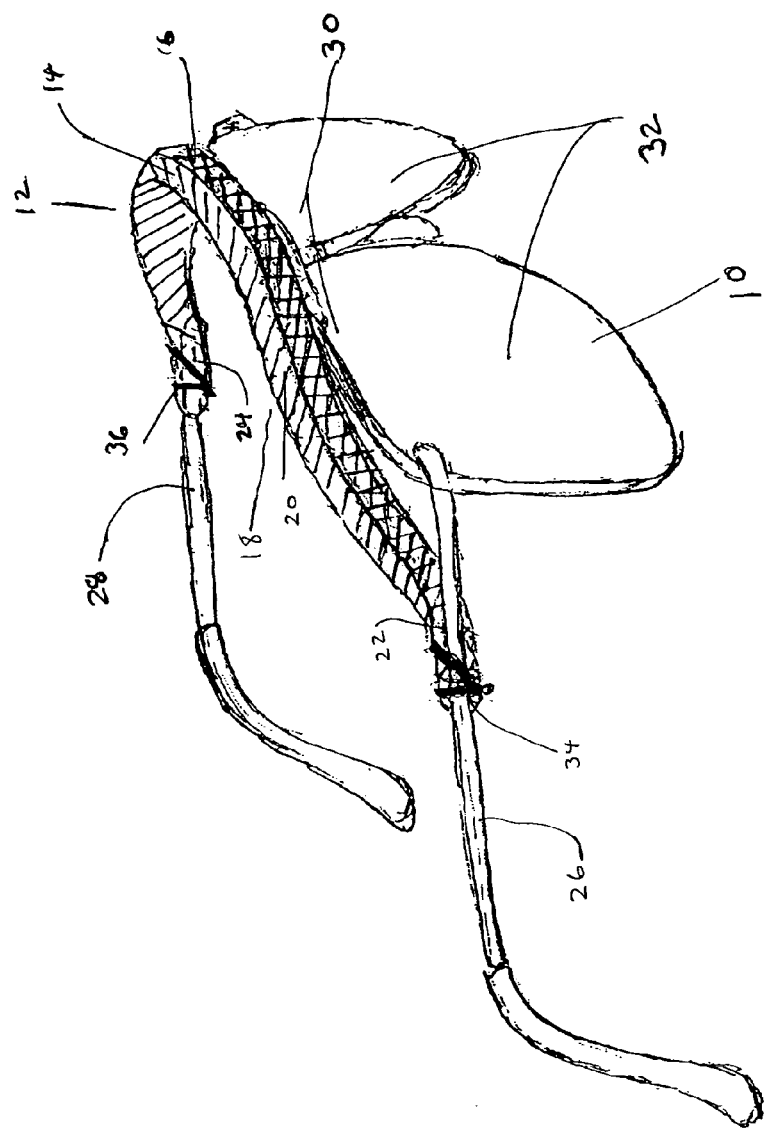
FIG. 1 is a perspective view of one embodiment of the apparatus, attached to eyeglasses.

As depicted in FIGS. 2 and 3, and also FIG. 1, the first piece 14 and second piece 16, when attached, together form a component 18 having a center portion 20 and a first end 22 and a second end 24. Each of the first end 22 and the second end 24 are attachable to the arms 26, 28 of eyeglasses 10, the center portion 20 of the component 18 being positioned proximate the top 30 of the eyeglass lenses 32, and oriented with the first piece 14 directed towards and in at least partial contact with the wearer's forehead. Any of several means for attaching the component 18 to the pair of eyeglasses 10 can be utilized. In one embodiment, the first end 22 and second end 24 of the component 18 are attachable to the arms 26, 28 of eyeglasses 10 with connecting means 34, 36 such as O-rings, or alternatively with rubber bands, rubber or plastic tubing, or elastic bands that encircle each of the first end 22 and second end 24 and the corresponding arms 26, 28 of the eyeglasses 10. In another embodiment, the connecting means 34, 36 includes clips, clasps, Velcro loops, ties, wires or other similar items connected to the first and second ends 22, 24 that are then attached to the arms 26, 28 of the eyeglasses 10. The use of clips and other similar connecting means facilitates quick and easy attachment and detachment of the first and second ends 22, 24 to and from the eyeglasses 10. It should be noted that the present apparatus may be useable with mono-lens goggles or safety glasses, as well as with eyeglasses or sunglasses with two lenses.

As depicted in FIGS. 2 and 3, one or more indentations 38, 40 are made in each of the first end 22 and the second end 24, which can assist in holding the connecting means 34, 36, such as an O-ring, in place around the arms 26, 28 of the eyeglasses 10. These indentations are omitted in alternative embodiments. The component 18 is positioned above the eyeglasses 10 such that the first piece 14, including the absorbent material, is brought into snug contact with the wearer's forehead. As will be appreciated, the positions of the first end 22 and second end 24 in relation to the arms 26, 28 of the eyeglasses 10 can be adjusted, so that the first end 22 and second end 24 are located along the eyeglass arms 26, 28 towards the wearer's ears in order to achieve a closer fit of the first piece 14 against the wearer's forehead. FIG. 4 depicts the embodiment of FIG. 1, showing the embodiment worn on the head of a person.

In the present embodiment, the first piece 14 is of a length approximately the width of the frame of the wearer's eyeglasses, although the first piece 14 can be of another length, including a length that causes the first piece 14 to wrap along the arms 26, 28 of the eyeglasses 10 and fully or partially around the wearer's temples. When worn by the wearer, the first piece 14 of the apparatus 12 is brought in full or partial contact with the user's forehead, so that it blocks and absorbs the flow of sweat, oils, dirt, sunscreen, and other materials that may flow down the wearer's forehead into the eyes or onto the wearer's eyeglasses 10. The first piece 14 also functions to direct the flow of moisture away from the wearer's eyes. The apparatus 12 also blocks dust and debris that may fall or blow into the wearer's eyes or onto the wearer's eyeglasses 10 from above the eyeglasses 10. The apparatus functions most advantageously to block dust and dirt when the center portion 20 is of a thickness to substantially fill the space between the eyeglass lenses (or monolens) and the wearer's forehead. In the present embodiment, this thickness is approximately one-half inch although in other embodiments the thickness can be varied.

As will be appreciated, the second piece 16 can be formed of any of various plastic materials, as well as other flexible and semi-rigid material, including leather and cloth. It can also be formed of a moldable material, such as a metal foil, or a bendable plastic or plastic with interior wire, that can be shaped to the wearer's forehead, and will tend to hold the shape and therefore provide a better fit. In one embodiment, and as depicted in FIGS. 1, 2 and 4, the component 18 is shaped in a downward bow shape, with the center portion 20 of the component 18, when worn, located higher on the wearer's forehead than the first and second ends 22, 24. This shape directs flow of excessive sweat and other liquid off the forehead and away from the wearer's eyes. In one embodiment, the second piece 16 is cut from a sheet of plastic having a thickness of about 1/64 of an inch. Other thicknesses may be used.

In the present embodiment, the first piece 14 is formed of absorbent material. In other embodiments, it can be formed of materials that are less absorbent or non-absorbent but that still impede, block or direct the flow of moisture. For example, the first piece can be formed of open cell or closed cell foam rubber. An open cell foam rubber acts as a sponge and absorbs moisture (although having some blocking and directing qualities, too), while closed cell foam rubber tends to impede flows of moisture and direct them off the wearer's forehead. Other absorbent or moisture-blocking material such as cloth, plastic, synthetic fiber material, or natural sponge material, can be used in place of foam rubber. Some materials may act to both absorb moisture and block and direct it away from the wearer's eyes. As will be appreciated, a variety of materials have been developed in the sports and recreational clothing industry that are breathable and that have wicking and moisture directing qualities, and it is contemplated that any of such materials may be used in the present apparatus.

Figure 5:
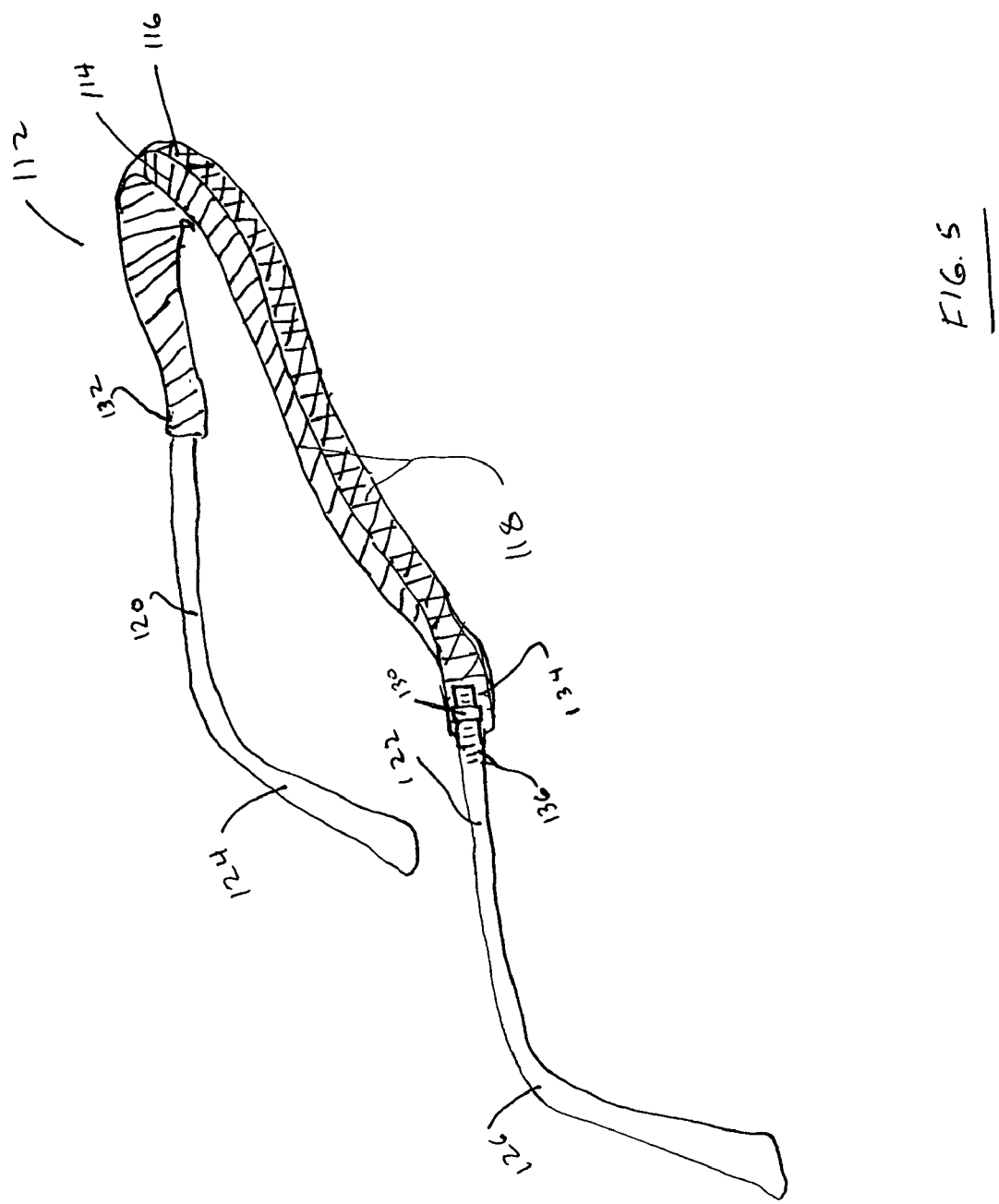
FIG. 5 is a perspective view of another embodiment of the apparatus.

In another embodiment, which can be worn independently of eyeglasses, the apparatus 112, depicted in FIG. 5, includes a first piece 114 and second piece 116 connected together forming a component 118 attachable to arms 120, 122. The arms 120, 122 are formed of any materials as are known in the field of eyeglasses, including metal, plastic or a combination of the two. The arms 120, 122 are structured to include earpieces 124, 126, although in other embodiments the ear pieces may be omitted (for example, where the arms are formed to hug the wearer's head). This embodiment of the apparatus 112 may be produced in various sizes to accommodate wearers' head sizes. The component 118 can be attached to the arms 120, 122 with attachment means 128, 130. In the present embodiment, shown in FIGS. 5, 6, 7, 8 and 9, the arms 120, 122 can be inserted into the attachment means 128, 130, which are attached to the first end 132 and second end 134 of the component 118. The attachment means 128, 130 hold the arms 120, 122 in place as depicted in FIG. 5. In the present embodiment, the arms 120, 122 each have grooves 136 which permit adjustable attachment of the arms 120, 122 to the attachment means 128, 130 of component 118. Other devices or components can be substituted for the attachment means 128, 130 depicted in FIGS. 5, 6, 7, 8, and 9, as are known in the field, such as O-rings, rubber or plastic tubing, rubber or elastic bands, or clips, clasps, mated snap-together connections, wires, and the like. The arms 120, 122 and attachment means 128, 130 can be configured so that the arms 120, 122 can be attached to the component 118 in one or more positions along the arms 120, 122, to provide a better fit of first piece 114 against the wearer's forehead.

In a further embodiment, the apparatus 112 can be produced and sold as a kit, including a component 118 and additional replacement components 118 and one or more pairs of arms 120, 122. In this embodiment, the wearer can readily detach the component 118 from the arms 120, 122 and replace the component 118 when soiled. In further embodiments, the component 118 is washable such that it can be re-used. The component 118 can then either be disposed or washed and reused. These embodiments of the apparatus 112, which include attachable arms 120, 122, can be worn by persons who do not wear eyeglasses, or can be worn along with eyeglasses, with the earpieces of the apparatus resting above the eyeglass earpieces on the wearer's ears.

An advantageous application of the apparatus is wearing the apparatus under a welder's helmet and face shield, the apparatus absorbing and impeding the flow of perspiration, oils and dirt down the wearer's face. Other advantageous applications are envisioned in fields where the wearer uses a face shield for prolonged periods, such as sports, dentistry and surgical medicine, the military, SWAT team and police forces, and the like.

Although the present invention has been described in considerable detail with reference to certain preferred embodiments, other embodiments are possible, and the spirit and scope of the appended claims should not be limited to the description of the preferred versions contained herein.

What is claimed is:

1. An apparatus for use with eyeglasses, said eyeglasses including a frame supporting a single lens or two lenses, and two arms, comprising:
   a first piece formed of an elongated sheet of liquid-absorbent material; and
   a second piece formed of a second elongated sheet of semi-rigid material of about the same size and shape as the first piece, the second piece being longitudinally connected to said first piece, and the first piece and second piece together forming a component having a center portion, a first end and a second end, each of the first end and second end being attachable to the arms of said eyeglasses, and the center portion of said component positioned proximate the top of said frame, and oriented with said first piece at least in partial contact with the forehead of the wearer of the eyeglasses, wherein said first piece is of a length of about the width of the frame of the eyeglasses.

2. The apparatus of claim 1, wherein the liquid-absorbent material is an open cell foam rubber.

3. The apparatus of claim 1, wherein the liquid-absorbent material is a cloth material.

4. The apparatus of claim 1, wherein the liquid absorbent material is a synthetic fiber material.

5. The apparatus of claim 1, wherein the liquid absorbent material is a sponge material.

6. The apparatus of claim 1, wherein the first piece is formed of an elongated sheet of material that is not substantially absorbent and that impedes and directs the flow of liquid on the wearer's forehead.

7. The apparatus of claim 6, wherein the first piece is formed from closed cell foam rubber.

8. The apparatus of claim 1, wherein the second piece is formed of a cloth material.

9. The apparatus of claim 1, wherein the second piece is formed of a plastic material.

10. The apparatus of claim 1, wherein the second piece is formed of a moldable material, that can be flexibly shaped to fit the wearer's forehead and thereafter retains its shape.

11. The apparatus of claim 1, wherein the component is shaped in an upside down bow shape for directing liquid away from the wearer's eyes.

12. The apparatus of claim 11, wherein said attachment means includes two clips, each encircling one of the first end and second end and one of the eyeglass arms.

13. The apparatus of claim 11, wherein said attachment means includes two O-rings, each O-ring encircling one of the first end and second end and one of the eyeglass arms.

14. The apparatus of claim 11, wherein said attachment means includes a loop lined with hook and loop fastener strips that encircles the first end and second end and the eyeglass arms.

15. The apparatus of claim 1, wherein said component is attached to said eyeglasses by an attachment means.

16. An apparatus for impeding flow of perspiration on the wearer's forehead, comprising:
 a first piece formed of an elongated sheet of liquid-absorbent material;
 a second piece formed of a second elongated sheet of semi-rigid material of about the same size and shape as the first piece, the second piece being longitudinally connected to the first piece, and the first piece and second piece together forming a component having a center portion, a first end and a second end, the first piece being directed towards the wearer's forehead;
 arms for attachment to each of said first end and said second end, each arm including an earpiece, for positioning on the wearer's ears; and
 attachment means, connected to each of said first end and second end for attaching and detaching said arms to said component.

17. The apparatus of claim 16, wherein the liquid-absorbent material is an open cell foam rubber.

18. The apparatus of claim 16, wherein the liquid-absorbent material is a cloth material.

19. The apparatus of claim 16, wherein the liquid absorbent material is a synthetic fiber materials.

20. The apparatus of claim 16, wherein the liquid-absorbent material is a sponge material.

21. The apparatus of claim 16, wherein the first piece is formed of an elongated sheet of material that impedes and directs the flow of liquid on the wearer's forehead.

22. The apparatus of claim 16, wherein the first piece is formed from closed cell foam rubber.

23. The apparatus of claim 16, wherein the second piece is formed of a cloth material.

24. The apparatus of claim 16, wherein the second piece is formed of a plastic material.

25. The apparatus of claim 16, wherein the second piece is formed of a moldable material, that can be flexibly shaped to fit the wearer's forehead and thereafter retains its shape.

26. A kit for a perspiration-impeding apparatus to be worn on a wearer's head, comprising:
 (a) a component formed of a first elongated sheet of liquid-absorbent material longitudinally connected to a second elongated sheet of semi-rigid material of about the same length and width as the first elongated sheet, the component having an attachment means on each of a first end and a second end of said component; and
 (b) arms attachable to said component at said attachment means on each of said first end and second end, said arms each having ear pieces for wearing over the wearer's ears, the component and said arms when attached together and worn by the wearer being positioned so that the first elongated sheet is in at least partial contact with the wearer's forehead.

27. The kit of claim 26, wherein said arms are attachable to said component in multiple locations, for fitting the arms and component to the wearer's ears and forehead.

28. The kit of claim 26, wherein said kit includes at least two arms and a plurality of components, wherein each of said components is attachable to said arms.

* * * * *